(12) United States Patent
Kolthammer et al.

(10) Patent No.: US 9,842,194 B2
(45) Date of Patent: Dec. 12, 2017

(54) SIMPLIFIED METHOD FOR ROBUST ESTIMATION OF PARAMETER VALUES

(71) Applicant: KONINKLIJKE PHILIPS N.V., Eindhoven (NL)

(72) Inventors: Jeffrey Allan Kolthammer, Cleveland Heights, OH (US); Raymond Frank Muzic, Jr., Mentor, OH (US)

(73) Assignees: KONINKLIJKE PHILIPS N.V., Eindhoven (NL); CASE WESTERN RESERVE UNIVERSITY, Cleveland, OH (US); UNIVERSITY HOSPITALS MEDICAL GROUP, INC., Cleveland, OH (US)

( * ) Notice: Subject to any disclaimer, the term of this patent is extended or adjusted under 35 U.S.C. 154(b) by 759 days.

(21) Appl. No.: 14/375,810

(22) PCT Filed: Feb. 8, 2013

(86) PCT No.: PCT/IB2013/051066
§ 371 (c)(1),
(2) Date: Jul. 31, 2014

(87) PCT Pub. No.: WO2013/121332
PCT Pub. Date: Aug. 22, 2013

(65) Prior Publication Data
US 2014/0365189 A1   Dec. 11, 2014

Related U.S. Application Data

(60) Provisional application No. 61/597,856, filed on Feb. 13, 2012.

(51) Int. Cl.
*G06F 7/60* (2006.01)
*G06F 17/10* (2006.01)
(Continued)

(52) U.S. Cl.
CPC .......... *G06F 19/3437* (2013.01); *A61B 6/037* (2013.01); *A61B 6/503* (2013.01);
(Continued)

(58) Field of Classification Search
CPC .................................................. G06F 19/3437
(Continued)

(56) References Cited

U.S. PATENT DOCUMENTS 6,963,670 B2   11/2005   Avinash et al.
7,706,397 B2    4/2010   Trainin et al.

FOREIGN PATENT DOCUMENTS

WO   2011138044 A1   11/2011

OTHER PUBLICATIONS

Boellaard, R., et al.; Evaluation of Basis Function and Linear Least Squares Methods for Generating Parametric Blood Flow Images Using 15O-Water and Positron Emission Tomography; 2005; Molecular Imaging Biology; 7(4) 273-285.
(Continued)

*Primary Examiner* — Timothy A Mudrick

(57) ABSTRACT

A method for estimating parameter values includes acquiring image data with an imaging apparatus, deriving a parameter model function from the image data, generating a N-dimensional grid, wherein N is a number of values of one or more non-linear terms of the derived model function, pre-calculating the one or more non-linear terms given the parameter model function and the designated values of the non-linear parameters, calculating one or more remaining model terms of the parameter model function, and displaying at least one of the one or more non-linear terms and remaining linear model terms.

18 Claims, 2 Drawing Sheets

(51) Int. Cl.
*G06F 19/00* (2011.01)
*A61B 6/00* (2006.01)
*G06T 7/00* (2017.01)
*G06F 17/50* (2006.01)
*A61B 6/03* (2006.01)

(52) U.S. Cl.
CPC ............ *A61B 6/507* (2013.01); *A61B 6/5217* (2013.01); *G06F 17/5009* (2013.01); *G06T 7/0016* (2013.01); *A61B 6/032* (2013.01); *G06T 2207/10016* (2013.01); *G06T 2207/10081* (2013.01); *G06T 2207/10084* (2013.01); *G06T 2207/10104* (2013.01); *G06T 2207/30104* (2013.01)

(58) Field of Classification Search
USPC .......................................................... 703/2
See application file for complete search history.

(56) References Cited

OTHER PUBLICATIONS

Lodge, M. A., et al.; Parametric Images of Blood Flow in Oncology PET Studies Using [15O] Water; 2000; The Journal of Nuclear Medicine; 41(11)1784-1792.

Lubberink, M., et al.; Low-Dose Quantitative Myocardial Blood Flow Imaging Using 15O-Water and PET Without Attenuation Correction; 2010; The Journal of Nuclear Medicine; 51(4)575-580.

Watabe, H., et al.; Parametric Imaging of Myocardial Blood Flow with 15O-Water and PET Using the Basis Function Method; 2005; The Journal of Nuclear Medicine; pp. 1219-1224.

SIMPLIFIED METHOD FOR ROBUST ESTIMATION OF PARAMETER VALUES

CROSS REFERENCE TO RELATED APPLICATIONS

This application is a national filing of PCI application Serial No. PCT/IB2013/051066 filed Feb. 8, 2013, published as WO 2013/121332 A1 on Aug. 22, 2013, which claims the benefit of U.& provisional application Ser. No. 61/597,856 filed Feb. 13, 2012, which is incorporated herein by reference.

The present application relates to the diagnostic imaging arts. It finds particular application in conjunction with estimating myocardial blood flow utilizing a nuclear medicine scanner and will be described with particular reference thereto. However, it is to be understood that it also finds application in other usage scenarios and is not necessarily limited to the aforementioned application.

In statistical parameter estimation, values of a set of unobservable parameters are estimated from measured data arising from a physical system. Systems in which the output is noisy or depends on the parameter in a nonlinear fashion make it particularly challenging to estimate these parameter values. Measurements from nuclear medicine images often fit this description. Presently, these measurements are used to estimate myocardial blood flow, metabolism of glucose or other substances, and the like with an iterative estimation technique to measure parameters of blood flow in the heart quantitatively, such as after a heart attack, partial or full occlusions of blood vessels, and the like.

However, estimating these parameter values is done through an iterative method. Such iterative methods are flexible but require a substantial amount of manual tuning including selection of initial guesses, boundary conditions, convergence criteria, optimization methods, objective functions, and the like. Additionally, iterative, nonlinear parameter estimation is computationally intense and its accuracy is difficult to characterize on unknown data. As such, performance is difficult to predict for a wide range of input data and large amounts of computations are often required. One example of such input data with which nonlinear estimation is a challenge is image-derived measurements of radioactivity in dynamic PET imaging. Typically, dynamic PET imaging data are used to estimate myocardial blood flow in humans and animals utilizing iterative solutions to nonlinear models. Further, linear solutions to parameter estimation only apply to linear models; in many cases, modeling the physical system with a linear model is an oversimplification or approximation. One example is the accumulation of a blood-flow tracer in the heart muscle Improving the accuracy and precision of such estimations and reducing their computation time are clinically important.

The present application provides new and improved methods and systems which overcome the above-referenced problems and others.

In accordance with one aspect, a method for estimating parameter values is provided. The method includes acquiring image data with an imaging apparatus, fitting a parameterized model function from the image data, generating a N-dimensional grid, wherein N is the number of one or more terms that are non-linear in a parameter of the derived model function, pre-calculating the one or more non-linear terms given the parameter model function and the designated values of the non-linear parameters, calculating one or more remaining model terms of the parameter model function, and displaying at least one of the one or more non-linear and remaining linear model terms.

In accordance with another aspect, a system for estimating a parameter is provided. The system includes an imaging apparatus which acquires data that is reconstructed to obtain images. A parameter estimation processor is programmed to derive a parameter model function from the image data, generate a N-dimensional grid, wherein N is a number of non-linear parameters or terms in the derived model function, and a multitude of values are designated along each dimension, pre-calculate the one or more non-linear terms given the parameter model function and the designated values of the non-linear parameters, calculate one or more remaining model terms of the parameter model function, and display at least one of the one or more non-linear and remaining, linear model terms.

In accordance with another aspect, a method for estimating myocardial blood flow is provided. The method includes calculating the product of a model input function and a non-linear function of a parameter k2, for each of a plurality of preselected values of k2, receiving image data with an imaging apparatus, calculating a myocardial blood flow model function y(t) from the image data, calculating an influx value K1 and a spillover value fv of the derived model function, selecting the optimal k2 value by minimizing an objective function, which measures the disagreement between the model output and experimental data, and displaying at least one of the influx K1, efflux k2, and spillover fv, or secondary values calculated from them on a display One advantage resides in improved accuracy and precision of parameter estimations.

Another advantage resides in improved computational efficiency of parameter estimation.

Another advantage resides in the separation of parameter estimation into computation parts which are solved as a linear solution.

Another advantage resides in avoiding calculations utilizing an iterative process, thereby avoiding unpredictable and local solutions and improving estimation robustness.

The invention may take form in various components and arrangements of components, and in various steps and arrangements of steps. The drawings are only for purposes of illustrating the preferred embodiments and are not to be construed as limiting the invention.

Figure 1:
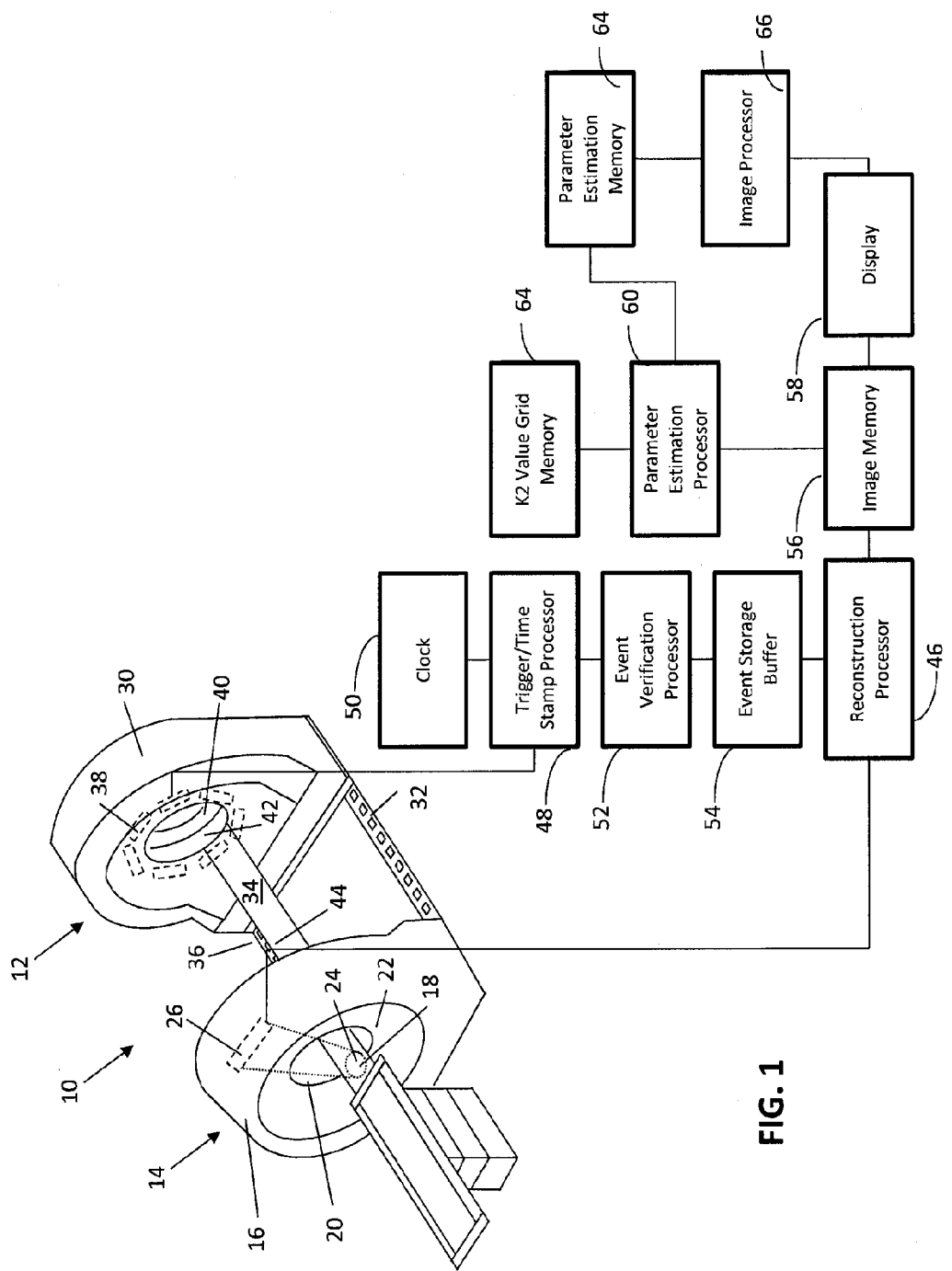
FIG. 1 is a diagrammatic illustration of a system for estimating parameter values in accordance with the present application.

With reference to FIG. 1, a multi-modality system 10 utilized to estimate myocardial flow is illustrated. Currently, myocardial flow estimation is performed with an iterative estimation technique to measure parameters of blood flow in the heart quantitatively. These blood flow parameters typically include the influx (K1), the efflux (k2), the spill-over (fv), and the like. Typically, these values are calculated approximating physiological parameters and utilizing a pharmacokinetic model.

In myocardial flow estimation, the amount of radiopharmaceutical in the blood of a subject and the amount of the radiopharmaceutical in the heart muscle of the subject is measured for each pixel in a region of an image. Measurements over time determine how fast the radiopharmaceutical is taken up by the heart muscle and how fast it passes from the heart muscle back into the blood of the subject. In practice, two or more time-sequences of images are typically generated, one with the heart at rest and one with the heart stressed. Pixel measurements are utilized to estimate the myocardial flow in the heart. The present application eliminates the iterative estimation of parameter values in favor of a simpler, more efficient, mathematical solution.

Specifically, the present application decomposes myocardial flow estimation calculations into a linear portion and a non-linear portion. In order to accomplish this, the nonlinear (k2 in one application) parts of the model equation are pre-calculated for values spanning the physiologic range. A grid of defined k2 values is stored, which spans a range of interest. For each such candidate value, the best K1 and fv values are determined in a closed-form solution by optimizing an objective function, which typically corresponds to minimizing the sum of squared differences between the pharmacokinetic model output and data. Optionally a weighted-sum could be used to account for differences in the relative importances of the various measurements.

With continued reference to FIG. 1, the multi-modality system 10 includes a first imaging system, e.g. a functional modality, preferably, a nuclear imaging system 12, and a second imaging system, e.g. an anatomical modality, such as a computed tomography (CT) scanner 14. The CT scanner 14 includes a non-rotating gantry 16. An x-ray tube or another source of x-rays 18 is mounted to a rotating gantry 20. A bore 22 defines an examination region 24 of the CT scanner 14. An array of radiation detectors 26 is disposed on the rotating gantry 20 to receive radiation from the x-ray tube 18 after the x-rays transverse the examination region 24. Alternatively, the array of detectors 26 may be positioned on the non-rotating gantry 16. Likewise, some scanner designs could include one or more stationary x-ray sources. Of course, magnetic resonance and other imaging modalities are also contemplated. The use of only a functional-modality imaging system, without a second imaging system, is also contemplated.

The functional or nuclear imaging system 12, in the illustrated embodiment, includes a positron emission tomography (PET) scanner 30 which may be mounted on tracks 32 to facilitate subject access. Of course, SPECT, CT, nuclear medicine imaging, and other imaging modalities are also contemplated. The tracks 32 extend in parallel to a longitudinal axis of a subject support or couch 34, thus enabling the CT scanner 14 and PET scanner 12 to form a closed system. A motor and drive 36, is provided to move the PET scanner 12 in and out of the closed position. Detectors 38 are arranged around a bore 40 which defines an examination region 42. In the illustrated PET system, the detectors 38 are arranged in a stationery ring, although rotatable or stationary heads or partial rings are also contemplated. In the SPECT system, the detectors 38 are typically incorporated into individual heads, which are mounted for rotational and radial movement relative to the subject. A motor and drive 44 or the like, provides a longitudinal movement and vertical adjustment of the subject support 34 in the examination regions 24, 42. Mounted CT and PET systems with a common examination region is also contemplated. As are MRI/PET systems, CT or MR/SPECT systems, C-arm X-ray CT/PET or SPECT system, and the like.

The subject support 34, which carries a subject, is moved into the examination region 24 of the CT scanner 14. The CT scanner 14 generates CT image data which is then used by a reconstruction processor 46 to generate a CT image. The reconstructed image is stored in an image memory 56 and displayed for a user on a display device 58, printed, saved for later use, and the like. The CT scanner 14 also generates radiation attenuated data in the form of an attenuation map which is then used by a reconstruction processor 46 to generate attenuated corrected image.

The subject support 34 then moves the subject into the PET scanner 12 in a position that is geometrically and mechanically predicated as being the same as the imaged position in the CT imaging region 24. Before the PET scan commences, the subject is injected with a one or more radiopharmaceuticals. The radiopharmaceuticals are commonly injected into the subject's blood stream for imaging the circulatory system or for imaging specific organs which absorb the injected radiopharmaceuticals. In the preferred embodiment, PET tracers for cardiac flow are used (ammonia, water, rubidium, or various labeled compounds, and the like). The radioisotope is used to measure the speed of chemical processes and to track the movement of a substance through a natural system such as a cell or tissue. It is also contemplated that other PET tracers for cardiac flow could be used, or other imaging modalities, or in areas other than the heart. After the patient has been injected, the patient undergoes a stress test (e.g., a treadmill exercise stress test) to aid in the evaluation of blood flow. It is also contemplated that the patient is injected during the stress test. The cardiac effect of exercise stress can also be simulated pharmacologically by the intravenous administration of a coronary vasodilator. Typically after administration of the radiotracer, the myocardium is imaged by the PET scanner 12. It is contemplated that the PET scanner 12 acquires a single image or a series of images. A second image or series of images is then obtained by the PET scanner 12 after an appropriate rest period. Alternatively, the patient may be given a second dose of the radiopharmaceutical during the rest phase and a second rest image or series of images is then acquired. Alternatively, the rest image or series of images may be acquired first, followed by instigation of the stress state, administration of radiopharmaceutical and then acquisition of a second stress image or series of images. Alternatively, the patient may only be studied in a resting state, or in a stressed state. The data collected from the series or multiple series of images is utilized to estimate absolute myocardial blood flow. The first image or series of images is also compared with the second image or series of images to determine both the functional capacity of coronary arteries in addition to the underlying viability of supplied myocardium.

In PET scanning, a pair of gamma rays is produced by a positron annihilation event in the examination region 42 and travel in opposite directions. When the gamma ray strikes the detectors 38, the location of the struck detector element and the strike time are recorded. A triggering processor 48 monitors each detector 38 for an energy spike, e.g., integrated area under the pulse, characteristic of the energy of the gamma rays generated by the radiopharmaceutical. The triggering processor 48 checks a clock 50 and stamps each detected gamma ray with a time of leading edge receipt stamp. In PET imaging, the time stamp, energy estimate and detector position estimation are first used by an event verification processor 52 to determine whether there is a coincident event. Accepted pairs of coincident events define lines of response (LORs). Once an event pair is verified by the event verification processor 52, the LOR is passed to an event storage buffer 54 with their time stamps are stored in the event storage buffer 54 as event data.

A reconstruction processor 46 reconstructs the LORs into an image representation of the subject. In one embodiment, a list-mode reconstruction algorithm is used. The reconstruction processor 46 reconstructs the image representation from the LORs by generating an image value for each voxel including the contribution of each LOR which intersects the voxel. The voxel can have a shape of a rectangular prism, e.g. a cube, a blob, or the like. The possible LORs are defined by the geometry of the scanner. In a PET scanner, a plurality of discrete detectors are disposed at fixed locations around the examination region to define discrete geometric points at which an LOR can terminate. In one embodiment, the reconstruction processor 46 accesses the attenuation map and generates an attenuation corrected reconstructed image. The reconstructed image is stored in an image memory 56 and displayed for a user on a display device 58, printed, saved for later use, and the like.

In one embodiment, a parameter estimation processor 60 utilizes the image data from the image representation and/or the attenuation corrected reconstructed image to estimate myocardial blood flow. Estimating myocardial blood flow has become a common practice in nuclear medicine applications and traditionally been performed with an iterative estimation technique to measure parameters of blood flow in the heart quantitatively. These techniques estimate myocardial blood flow in subjects iteratively and utilizing nonlinear models. As mentioned above, some previous pharmacokinetic models for blood flow include three parameters: influx K1, efflux k2, and spillover fv. After administering a radioactive compound into the subject, the radioactive compound migrates from the blood of the subject into the tissue compartment. Influx K1 represents the rate of inflow of the radioactive compound into the tissue compartment whereas efflux k2 represents the rate of outflow of the radioactive compound from the tissue compartment. The accumulated radioactivity x(t) contributes to the measured data acquired during uptake and washout of the radiopharmaceutical. The accumulated radioactivity x(t) in the model tissue compartment at time t is represented by the following equation.

$$x(t) = \int_{T=0}^{t} e^{[-k_2(t-T)]} K_1 u(T) \, dT \quad (1)$$

wherein x(t) is the accumulated activity, t is a time since the radiopharmaceutical was injected, k2 is the efflux, K1 is the influx, and u(t) is the input activity. The values y(t) of the image data acquired by the PET scanner are described by the following formula.

$$y(t) = f_v v(t) + (1-f_v) x(t) \quad (2)$$

wherein y(t) is the image data, fv is the spillover fraction, v(t) is the spillover activity, which may be the same as the input activity, and x(t) is the accumulated tissue compartment activity. As shown in the above formulas, efflux k2 is in an exponent and therefore x(t), and thus model output y(t), have a nonlinear dependence on k2. Traditionally, such a non-linear equation is solved by the iterative parameter estimation described above. Such iterative, nonlinear parameter estimation is computationally inefficient and its accuracy is difficult to predict. Equation (2) is written as an illustration with a single spillover fraction and spillover activity, although similar model equations combing multiple fractions and activities are contemplated.

To improve the accuracy, precision and robustness of such estimations, the structure the above formulas can be combined and broken into a non-linear portions (the term containing k2) and a linear portion (terms containing K1 and fv). The model equation is separated as follows, in which the integral term includes only k2 but not the other parameters.

$$y(t) = [X][A] = \begin{bmatrix} v(t) & \int_{T=0}^{t} e^{[-k_2(t-T)]} K_1 u(T) \, dT \\ \vdots & \vdots \end{bmatrix} \begin{bmatrix} f_v \\ (1-f_v) K_1 \end{bmatrix} \quad (3)$$

wherein y(t) is the model output, u(t) is an input activity, v(t) is a spillover activity, fv is the spillover fraction, K1 is the influx constant, k2 is the efflux constant, [v(t) ∫ . . . ], in which each term has one or more vertical elements, is [X], and $$\begin{bmatrix} f_v \\ (1-f_v) K_1 \end{bmatrix}$$

is [A]. Additional embodiments are contemplated in which the illustrated method is applied to a multitude of compartments, and a multitude of spillover fractions representing spillover from different sources.

This enables parameter estimation to be conducted in a sequence of closed-form computational steps rather than utilizing an iterative method. After imaging a patient, matrix [X] calculated over a range of typical efflux k2 values and stored in a parameter estimation memory 62. When the model output y(t) is generated, the values of influx constant K1 and spillover fraction fv are calculated for each of an array of the k2 values by using the pre-calculated matrix [X].

In one embodiment, a grid of k2 values is set up prior to imaging a current patient. When the scanner is manufactured or prior to imaging a current patient, the grid of specified values of k2 is stored in a k2 value grid or other suitable memory 64. In other words, a grid or matrix of a range of possible k2 values of a human subject is generated. To achieve clinically meaningful results k2 is preferably sampled at sufficient frequency such that its discretization does not contribute significantly to the total estimation error. In humans k2 is typically between 0 and 1 min$^{-1}$. Accordingly, working with about 100 potential k2 values is normally clinically adequate. For each specified value of k2, the matrix [X] is calculated. After matrix [X] is calculated, matrix [A] is calculated for each pixel or region of interest utilizing the precalculated values of matrix [X] and the image data acquired from the PET scanner. The values of K1 and fv are then calculated from matrix [A] and without need of recalculating X for each pixel or each region of interest. The overall parameter estimation result is extracted from the results of the calculation of K1 and fv. All or intelligently selected values of k2 are sampled and each value of K1 and fv for each value of k2 is calculated. In one embodiment, the optimal k2 values are selected by minimizing the sum squared differences between the data and the model output at each set of K1, fv, and k2 values. It is contemplated utilizing an iterative method for determining the optimal k2 value. It is also contemplated resampling the k2 values at finer intervals to determine the optimal k2 values. The subsequent calculations are repeated for each voxel or region of interest of the image data, and the values of neighboring voxels can be used to expedite the error minimization.

In one embodiment, the values of K1, fv, and k2, or values calculated therefrom, are each displayed in a color or gray scale overlaying a corresponding 2D image, or 3D volumetric image, such as the CT image, on the display 58. Specifically, an image processor 66 retrieves the K1, k2, and fv values and generates the visualization on the display 58. It is also contemplated that the image processor 66 colorizes a 17 segment display model or other standardized model or template. In another embodiment, each voxel of the image is displayed with varying color or grayscale representations to indicate different myocardial flow values. It is also contemplated that the display enables a user to select a particular area or region of interest of the image and display the average K1 and k2 values for that particular region. In another embodiment, the display illustrates the blood flow during a resting period and the blood flow during an active period and the difference between the periods shown in a color representation. In the one embodiment, each segment of a standard 17-segment cardiac model is fit independently. The whole myocardium could be fit, or each of several segments or regions, or each voxel in the heart independently.

The above parameter estimation process is implemented in software and lends itself toward other (e.g. hardware, or GPU) implementations. The key feature of the parameter estimation is performed in a closed-form (non-iterative) calculation, and that the nonlinear portion of the problem is moved outside the estimation step via a grid or table search. This reduces the dimensionality of the space that must be iteratively evaluated in order to determine the values of the parameters.

The reconstruction processor 46, triggering processor 48, event verification processor 52, parameter estimation processor 60, and image processor 66 include a processor, for example a microprocessor or other software controlled device configured to execute image reconstruction software for performing the operations described in further detail below. Typically, the image reconstruction software is carried on tangible memory or a computer readable medium for execution by the processor. Types of computer readable media include memory such as a hard disk drive, CD-ROM, DVD-ROM and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

Figure 2:
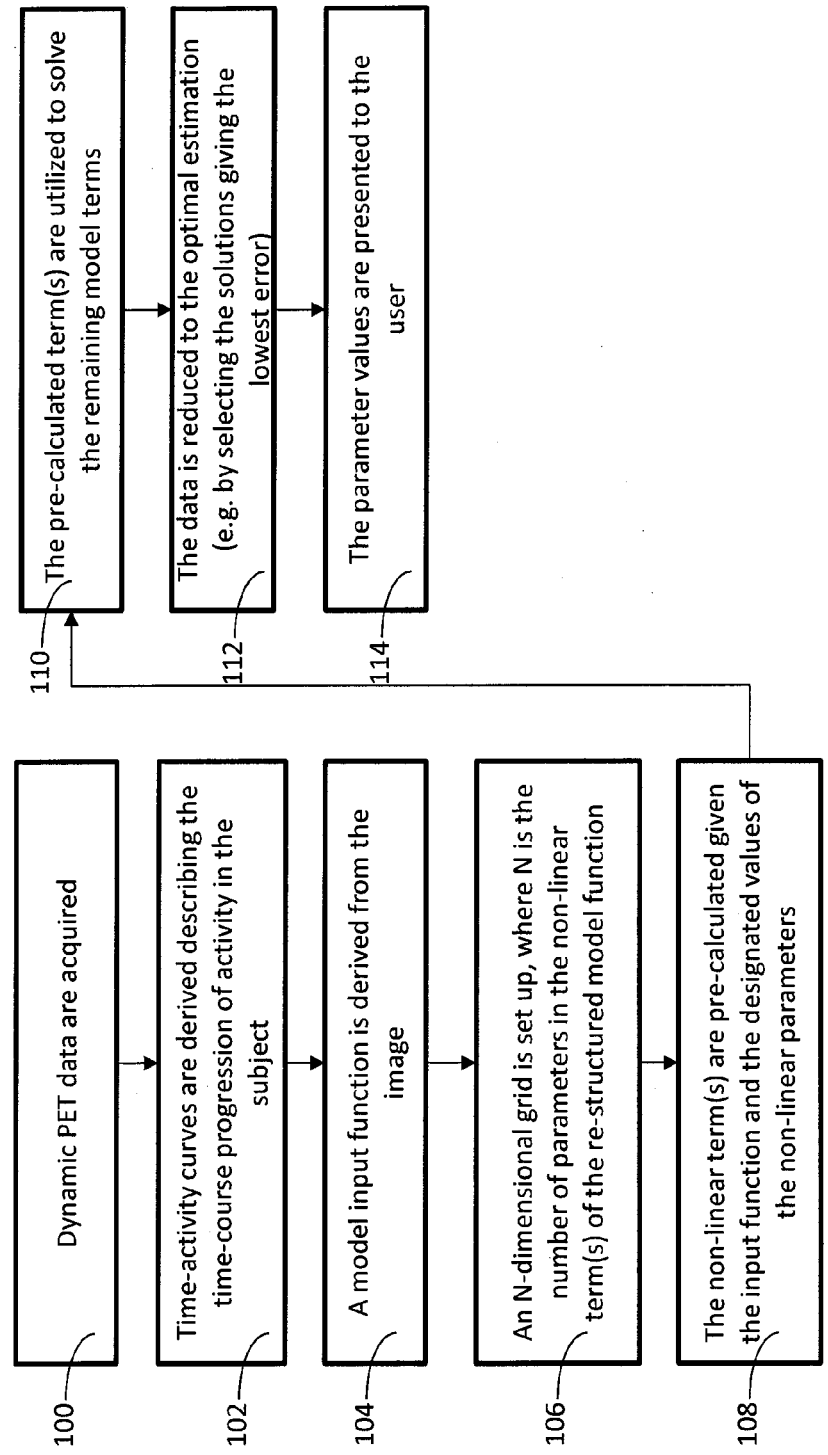
FIG. 2 is a flowchart illustration of a method of estimating parameter values in accordance with the present application.

FIG. 2 illustrates a method of image processing. In a step 100, dynamic PET data are acquired. Time-activity curves are derived describing the time-course progression of activity in the subject in a step 102. In a step 104, a model input function is derived from the image. In a step 106, an N-dimensional grid is set up, where N is the number of parameters in the non-linear term(s) of the re-structured model function and a series of parameter values is designated for each of the N parameters. In a step 108, pre-calculate the non-linear term(s), given the input function and the designated values of the non-linear parameters. In a step 110, the pre-calculated term(s) are utilized to solve the remaining model terms. In a step 112, the data is reduced to the optimal estimation (e.g. by selecting the solutions giving the lowest error). In a step 114, the parameter values are presented to the user. In the implemented embodiment, the steps are done in sequence. It is also contemplated that the steps could be done in parallel utilizing parallel processing using a multicore, multiprocessor, cluster or GPU approach.

For example, a method for estimating myocardial blood flow includes the steps of acquiring image data with an imaging apparatus. A myocardial blood flow model function is derived from the image data. An N-dimensional grid is generated, wherein a multitude of values of each of N non-linear parameters of the derived model function are designated. An influx value and a spillover value of the derived model function are calculated. At least one of the efflux constant, influx constant, and spillover fraction are displayed.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for estimating parameter values comprising:
obtaining image data with an imaging apparatus;
fitting a parameterized model function utilized to estimate myocardial blood flow and representing spillover by a scaling factor $$\left[\frac{f_v}{(1-f_v)K_1}\right]$$

where $f_v$ is a spillover fraction and $K_1$ is an influx value from the image data by:
generating a N-dimensional grid, wherein N is a number of one or more terms that are non-linear in a parameter of the derived model function;
pre-calculating the one or more non-linear terms given the parameter model function and the designated values of the non-linear parameters;
calculating one or more remaining model terms of the parameter model function; and
displaying at least one of the one or more non-linear and remaining linear model terms.

2. The method according to claim 1, wherein the parameter model function is represented by $$y(t) = \left[v(T)\int e^{[-k_2(t-T)]}dT\right]\left[\frac{f_v}{(1-f_v)K_1}\right],$$

wherein y(t) is the image data model, u(t) is an input activity, v(t) is a spillover activity, and k2 is an efflux value.

3. The method according to claim 2, wherein the one or more non-linear terms of the derived model function include values of k2.

4. The method according to claim 3, wherein the K1 value and fv value are calculated for each of the values of k2.

5. The method according to claim 1, further including:
optimizing the non-linear terms by minimizing error.

6. The method according to claim 1, wherein the at least one of the one or more non-linear terms and one or more remaining model terms are displayed on utilizing a standardized display model.

7. A non-transitory computer readable medium which carries a computer program which controls one or more processors to perform the method of claim 1.

8. A system for estimating a parameter, the system comprising:
an imaging apparatus which obtains data that is reconstructed to obtain images;
a parameter estimation processor programmed to:
derive a parameter model function from the image data in which spillover is represented by a scaling factor $$\left[\frac{f_v}{(1-f_v)K_1}\right]$$

where $f_v$ is a spillover fraction and $K_1$ is an influx value;

generate a N-dimensional grid, wherein N is a number of non-linear parameters or terms in the derived model function and a plurality of values are designated along each dimension;

pre-calculate the one or more non-linear terms given the parameter model function and the designated values of the non-linear parameters;

calculate one or more remaining model terms of the parameter model function; and display at least one of the one or more non-linear and remaining, linear model terms.

9. The system according to claim 8, wherein the parameter model function is utilized to estimate myocardial blood flow.

10. The system according to claim 9, wherein the parameter model function is represented by $$y(t) = \left[v(T)\int e^{[-k_2(t-T)]}dt\right]\left[\frac{f_v}{(1-f_v)K_1}\right],$$

wherein y(t) is the image data, v(t) is a spillover activity, and k2 is an efflux value.

11. The system according to claim 10, wherein the one or more non-linear terms of the derived model function include values of k2.

12. The system according to claim 11, wherein the K1 value and fv value are calculated for each of values of k2.

13. The system according to claim 8, wherein the parameter estimation processor is further programmed to:

optimize the non-linear terms by minimizing an error term.

14. The system according to claim 8, wherein the at least one of the one or more non-linear terms and one or more remaining model terms are displayed on utilizing a standardized display model.

15. A method for estimating myocardial blood flow, the method comprising:

calculating x(t) for each of a plurality of preselected values of k2;

obtaining image data with an imaging apparatus;

deriving a myocardial blood flow model function y(t) from the image data wherein the myocardial blood flow model function y(t) is represented by:

$$\left[v(T)\int e^{[-k_2(t-T)]}dT\right]\left[\frac{f_v}{(1-f_v)K_1}\right]$$

wherein y(t) is the image data, v(t) is a spillover activity, fv is a spillover value, K1 is an influx value, and k2 is an efflux value;

calculating an influx value K1 and a spillover value fv of the derived model function;

optimizing the k2 values by minimizing the error; and displaying at least one of the efflux K1, influx k2, and spillover fv on a display.

16. The method according to claim 15, wherein the at least one of the efflux, influx, and spillover are displayed on a segment display model.

17. A non-transitory computer readable medium which carries a computer program which controls one or more processors to perform the method of claim 15.

18. A system for estimating myocardial blood flow, the system comprising:

one or more processor programmed to perform the method of claim 15;

at least one of a display for displaying and a memory for storing k2, K1, and fv.

* * * * *